(12) United States Patent
Ethridge et al.

(10) Patent No.: US 11,963,893 B2
(45) Date of Patent: Apr. 23, 2024

(54) ESOPHAGEAL STENTS WITH HELICAL THREAD

(71) Applicant: Merit Medical Systems, Inc., South Jordan, UT (US)

(72) Inventors: Tiffany Ethridge, Lubbock, TX (US); Zeke Eller, Plano, TX (US); Bryan K. Elwood, Arlington, TX (US)

(73) Assignee: Merit Medical Systems, Inc., South Jordan, UT (US)

( * ) Notice: Subject to any disclaimer, the term of this patent is extended or adjusted under 35 U.S.C. 154(b) by 185 days.

(21) Appl. No.: 17/509,749

(22) Filed: Oct. 25, 2021

(65) Prior Publication Data
US 2022/0125608 A1 Apr. 28, 2022

Related U.S. Application Data

(60) Provisional application No. 63/105,747, filed on Oct. 26, 2020.

(51) Int. Cl.
*A61F 2/88* (2006.01)
*A61F 2/90* (2013.01)
A61F 2/04 (2013.01)

(52) U.S. Cl.
CPC .......... *A61F 2/88* (2013.01); *A61F 2/90* (2013.01); *A61F 2002/044* (2013.01); *A61F 2230/0091* (2013.01)

(58) Field of Classification Search
CPC .... A61F 2/88; A61F 2/90; A61F 2/064; A61F 2/07; A61F 2002/072; A61F 2230/0091; A61F 2230/0069; A61F 2250/0039
See application file for complete search history.

(56) References Cited

U.S. PATENT DOCUMENTS

| | | | |
|---|---|---|---|
| 4,913,141 A | 4/1990 | Hillstead |
| 5,201,757 A | 4/1993 | Heyn et al. |
| 5,413,575 A | 5/1995 | Haenggi |
| 5,534,007 A | 7/1996 | Germain et al. |
| 5,591,172 A | 1/1997 | Bachmann et al. |
| 5,591,196 A | 1/1997 | Marin et al. |
| 5,603,698 A | 2/1997 | Roberts et al. |
| 5,645,559 A | 7/1997 | Hachtman et al. |
| 5,733,325 A | 3/1998 | Robinson et al. |

(Continued)

FOREIGN PATENT DOCUMENTS

| | | |
|---|---|---|
| CN | 210185778 | 3/2020 |
| DE | 4323866 | 1/1994 |

(Continued)

OTHER PUBLICATIONS

International Search Report and Written Opinion dated Jan. 9, 2018 for PCT/US2017/054000.

(Continued)

*Primary Examiner* — Paul B Prebilic
(74) *Attorney, Agent, or Firm* — Dorsey & Whitney LLP

(57) ABSTRACT

Stents as described herein can comprise a tubular body in which a midbody extends to a first end and also extends to an opposing second end, where the midbody includes a thread arranged helically along at least a portion of its length. The thread can exhibit various shapes and dimensions selected to enhance particular aspects of performance when the stent placed in an anatomical structure of a patient.

20 Claims, 9 Drawing Sheets

(56) References Cited

U.S. PATENT DOCUMENTS

| | | |
|---|---|---|
| 5,755,769 A | 5/1998 | Richard et al. |
| 5,759,186 A | 6/1998 | Bachmann et al. |
| 5,824,041 A | 10/1998 | Lenker et al. |
| 5,868,755 A | 2/1999 | Kanner et al. |
| 5,876,448 A | 3/1999 | Thompson et al. |
| 5,916,147 A | 6/1999 | Boury |
| 5,944,727 A | 8/1999 | Ahari et al. |
| 5,968,052 A | 10/1999 | Sullivan, III et al. |
| 6,015,429 A | 1/2000 | Lau et al. |
| 6,093,194 A | 7/2000 | Mikus et al. |
| 6,123,715 A | 9/2000 | Amplatz |
| 6,143,021 A | 11/2000 | Staehle |
| 6,146,415 A | 11/2000 | Fitz |
| 6,162,231 A | 12/2000 | Mikus et al. |
| 6,241,757 B1 | 6/2001 | An et al. |
| 6,270,524 B1 | 8/2001 | Kim |
| 6,283,992 B1 | 9/2001 | Hankh et al. |
| 6,368,339 B1 | 4/2002 | Amplatz |
| 6,383,211 B1 | 5/2002 | Staehle |
| 6,391,051 B2 | 5/2002 | Sullivan, III et al. |
| 6,413,269 B1 | 7/2002 | Bui et al. |
| 6,416,545 B1 | 7/2002 | Mikus et al. |
| 6,428,566 B1 | 8/2002 | Holt |
| 6,443,980 B1 | 9/2002 | Wang et al. |
| 6,447,531 B1 | 9/2002 | Amplatz |
| 6,514,261 B1 | 2/2003 | Randall et al. |
| 6,520,983 B1 | 2/2003 | Colgan et al. |
| 6,530,933 B1 | 3/2003 | Yeung et al. |
| 6,599,296 B1 | 7/2003 | Gillick et al. |
| 6,599,308 B2 | 7/2003 | Amplatz |
| 6,613,079 B1 | 9/2003 | Wolinsky et al. |
| 6,616,675 B1 | 9/2003 | Evard et al. |
| 6,629,981 B2 | 10/2003 | Dennis et al. |
| 6,645,143 B2 | 11/2003 | Vantassel et al. |
| 6,669,719 B2 | 12/2003 | Wallace et al. |
| 6,726,712 B1 | 4/2004 | Raeder-Devens et al. |
| 6,746,480 B2 | 6/2004 | Scholz et al. |
| 6,770,101 B2 | 8/2004 | Desmond, III et al. |
| 6,776,791 B1 | 8/2004 | Jody et al. |
| 6,821,295 B1 | 11/2004 | Farrar |
| 6,866,669 B2 | 3/2005 | Buzzard et al. |
| 6,893,413 B2 | 5/2005 | Martin |
| 6,926,732 B2 | 8/2005 | Derus et al. |
| 6,955,685 B2 | 10/2005 | Escamilla et al. |
| 7,004,966 B2 | 2/2006 | Edwin et al. |
| 7,083,640 B2 | 8/2006 | Lombardi et al. |
| 7,309,350 B2 | 12/2007 | Landreville et al. |
| 7,309,351 B2 | 12/2007 | Escamilla et al. |
| 7,335,224 B2 | 2/2008 | Ohlenschaeger |
| 7,393,357 B2 | 7/2008 | Stelter et al. |
| 7,473,271 B2 | 1/2009 | Gunderson |
| 7,591,848 B2 | 9/2009 | Allen |
| 7,637,942 B2 | 12/2009 | Mangiardi et al. |
| 7,731,654 B2 | 6/2010 | Mangiardi et al. |
| 7,959,671 B2 | 6/2011 | Mangiardi et al. |
| 8,012,194 B2 | 9/2011 | Edwin et al. |
| 8,206,436 B2 | 6/2012 | Mangiardi et al. |
| 8,262,719 B2 | 9/2012 | Erickson et al. |
| 8,357,193 B2 | 1/2013 | Phan et al. |
| 8,414,635 B2 | 4/2013 | Hyodoh et al. |
| 8,425,539 B2 | 4/2013 | Binmoeller et al. |
| 8,439,934 B2 | 5/2013 | Satasiya et al. |
| 8,454,632 B2 | 6/2013 | Binmoeller et al. |
| 8,518,099 B2 | 8/2013 | Chanduszko et al. |
| 8,524,132 B2 | 9/2013 | Von Oepen et al. |
| 8,535,366 B2 | 9/2013 | Mangiardi et al. |
| 8,652,099 B2 | 2/2014 | Fierens et al. |
| 8,677,874 B2 | 3/2014 | Lilburn et al. |
| 8,696,611 B2 | 4/2014 | Yaacov et al. |
| 8,715,334 B2 | 5/2014 | Clerc et al. |
| 8,834,558 B2 | 9/2014 | Nissl |
| 8,906,081 B2 | 12/2014 | Cully et al. |
| 8,926,683 B2 | 1/2015 | Darla et al. |
| 9,107,741 B2 * | 8/2015 | Bui ................. A61F 2/856 |
| 9,155,643 B2 | 10/2015 | Clerc et al. |
| 9,192,496 B2 | 11/2015 | Robinson |
| 9,259,336 B2 | 2/2016 | Schaeffer et al. |
| 9,284,637 B2 | 3/2016 | Boyle et al. |
| 9,381,041 B2 | 7/2016 | Brown et al. |
| 10,285,834 B2 | 5/2019 | Cindrich et al. |
| 2001/0037141 A1 | 11/2001 | Yee et al. |
| 2002/0068037 A1 | 6/2002 | Platzet et al. |
| 2002/0138095 A1 | 9/2002 | Mazzocchi et al. |
| 2002/0151967 A1 | 10/2002 | Mikus et al. |
| 2002/0183827 A1 | 12/2002 | Derus et al. |
| 2002/0193749 A1 | 12/2002 | Olovson |
| 2003/0023268 A1 | 1/2003 | Lizardi |
| 2003/0028236 A1 | 2/2003 | Gillick |
| 2003/0050686 A1 | 3/2003 | Raeder-Devens et al. |
| 2003/0135265 A1 | 7/2003 | Stinson |
| 2003/0135268 A1 | 7/2003 | Desai |
| 2003/0144671 A1 | 7/2003 | Brooks et al. |
| 2003/0167060 A1 | 9/2003 | Buzzard et al. |
| 2004/0030381 A1 | 2/2004 | Shu |
| 2004/0098077 A1 | 5/2004 | Gianotti |
| 2004/0127973 A1 | 7/2004 | Mangiardi et al. |
| 2004/0181239 A1 | 9/2004 | Dorn et al. |
| 2004/0193243 A1 | 9/2004 | Mangiardi et al. |
| 2004/0267281 A1 | 12/2004 | Harari et al. |
| 2005/0027345 A1 | 2/2005 | Horan et al. |
| 2005/0038495 A1 | 2/2005 | Greenan |
| 2005/0090887 A1 | 4/2005 | Pryor |
| 2005/0125050 A1 | 6/2005 | Carter et al. |
| 2005/0149160 A1 | 7/2005 | McFerran |
| 2005/0182475 A1 | 8/2005 | Jen et al. |
| 2005/0278010 A1 | 12/2005 | Richardson |
| 2005/0283179 A1 | 12/2005 | Lentz |
| 2006/0020321 A1 | 1/2006 | Parker |
| 2006/0155368 A1 | 7/2006 | Shin |
| 2006/0184224 A1 | 8/2006 | Angel |
| 2006/0258972 A1 | 11/2006 | Mangiardi et al. |
| 2006/0259113 A1 | 11/2006 | Nissl |
| 2007/0005122 A1 | 1/2007 | Inoue |
| 2007/0043421 A1 | 2/2007 | Mangiardi et al. |
| 2007/0100421 A1 | 5/2007 | Griffin |
| 2007/0135904 A1 | 6/2007 | Eidenschink et al. |
| 2007/0156225 A1 | 7/2007 | George et al. |
| 2007/0179590 A1 | 8/2007 | Lu et al. |
| 2007/0208350 A1 | 9/2007 | Gunderson |
| 2007/0250150 A1 | 10/2007 | Pal et al. |
| 2007/0270932 A1 | 11/2007 | Headley et al. |
| 2008/0114443 A1 | 5/2008 | Mitchell et al. |
| 2008/0140178 A1 | 6/2008 | Rasmussen et al. |
| 2008/0228256 A1 * | 9/2008 | Erickson ................. D04C 1/06<br>623/1.11 |
| 2008/0288042 A1 | 11/2008 | Purdy et al. |
| 2009/0099636 A1 | 4/2009 | Chanduszko et al. |
| 2009/0099647 A1 | 4/2009 | Glimsdale et al. |
| 2009/0118740 A1 | 5/2009 | Mangiardi et al. |
| 2009/0157158 A1 | 6/2009 | Ondracek |
| 2009/0171427 A1 | 7/2009 | Melsheimer et al. |
| 2009/0171433 A1 | 7/2009 | Melsheimer |
| 2009/0187240 A1 | 7/2009 | Clerc |
| 2009/0192518 A1 | 7/2009 | Golden et al. |
| 2009/0292262 A1 | 11/2009 | Adams et al. |
| 2010/0023032 A1 | 1/2010 | Granja et al. |
| 2010/0023132 A1 | 1/2010 | Imran |
| 2010/0030256 A1 | 2/2010 | Dubrul et al. |
| 2010/0030321 A1 | 2/2010 | Mach |
| 2010/0049295 A1 | 2/2010 | Satasiya et al. |
| 2010/0057145 A1 | 3/2010 | Bhatnagar et al. |
| 2010/0057185 A1 | 3/2010 | Melsheimer et al. |
| 2010/0070016 A1 | 3/2010 | Dorn |
| 2010/0145431 A1 | 6/2010 | Wu et al. |
| 2010/0252470 A1 | 10/2010 | Ryan et al. |
| 2011/0004290 A1 | 1/2011 | Bales, Jr. et al. |
| 2011/0015616 A1 | 1/2011 | Straubinger et al. |
| 2011/0082464 A1 | 4/2011 | Douk et al. |
| 2011/0137396 A1 | 6/2011 | Dorn et al. |
| 2011/0137400 A1 | 6/2011 | Dorn et al. |
| 2011/0190862 A1 | 8/2011 | Bashiri et al. |
| 2011/0208296 A1 | 8/2011 | Duffy et al. |
| 2011/0264191 A1 | 10/2011 | Rothstein |
| 2011/0288482 A1 | 11/2011 | Farrell et al. |

(56) References Cited

U.S. PATENT DOCUMENTS

| | | |
|---|---|---|
| 2011/0307070 A1 | 12/2011 | Clerc et al. |
| 2011/0319980 A1 | 12/2011 | Ryan |
| 2012/0046729 A1 | 2/2012 | Von Oepen et al. |
| 2012/0095567 A1 | 4/2012 | Weisman et al. |
| 2012/0136426 A1 | 5/2012 | Phan et al. |
| 2012/0290066 A1 | 11/2012 | Nabulsi et al. |
| 2012/0296257 A1 | 11/2012 | Van Dan et al. |
| 2012/0303109 A1 | 11/2012 | Okuma |
| 2012/0303112 A1 | 11/2012 | Armstrong et al. |
| 2012/0310320 A1 | 12/2012 | Gill et al. |
| 2013/0018215 A1 | 1/2013 | Snider et al. |
| 2013/0103163 A1 | 4/2013 | Krimsky et al. |
| 2013/0110221 A1 | 5/2013 | Campbell et al. |
| 2013/0116770 A1 | 5/2013 | Robinson |
| 2013/0116771 A1 | 5/2013 | Robinson |
| 2013/0116772 A1 | 5/2013 | Robinson et al. |
| 2013/0158673 A1 | 6/2013 | Toomey |
| 2013/0184833 A1 | 7/2013 | Ryan et al. |
| 2013/0197623 A1 | 8/2013 | McHugo |
| 2013/0231689 A1 | 9/2013 | Binmoeller et al. |
| 2013/0253546 A1 | 9/2013 | Sander et al. |
| 2013/0274870 A1 | 10/2013 | Lombardi et al. |
| 2013/0310833 A1 | 11/2013 | Brown et al. |
| 2014/0074065 A1 | 3/2014 | Muni et al. |
| 2014/0074219 A1 | 3/2014 | Hingston et al. |
| 2014/0171863 A1 | 6/2014 | Blacker |
| 2014/0236064 A1 | 8/2014 | Binmoeller et al. |
| 2014/0243992 A1 | 8/2014 | Walsh et al. |
| 2014/0277573 A1 | 9/2014 | Gill et al. |
| 2014/0288636 A1 | 9/2014 | Headley, Jr. et al. |
| 2014/0303709 A1 | 10/2014 | Dwork |
| 2014/0330305 A1 | 11/2014 | Rood et al. |
| 2014/0350694 A1 | 11/2014 | Behan |
| 2014/0364959 A1 | 12/2014 | Attar et al. |
| 2015/0066128 A1 | 3/2015 | Losordo et al. |
| 2015/0100133 A1 | 4/2015 | Xie et al. |
| 2015/0112377 A1 | 4/2015 | Arnone et al. |
| 2015/0173919 A1 | 6/2015 | Baldwin |
| 2015/0230955 A1 | 8/2015 | Farag Eells et al. |
| 2015/0313595 A1 | 11/2015 | Houshton et al. |
| 2015/0313599 A1 | 11/2015 | Johnson et al. |
| 2016/0081823 A1 | 3/2016 | Majercak |
| 2016/0081832 A1 | 3/2016 | Hingston et al. |
| 2016/0242846 A1 | 8/2016 | Brown et al. |
| 2016/0256306 A1 | 9/2016 | Cindrich et al. |
| 2017/0014133 A1 | 1/2017 | Han et al. |
| 2017/0035424 A1 | 2/2017 | Binmoeller et al. |
| 2017/0035426 A1 | 2/2017 | Phan et al. |
| 2017/0035427 A1 | 2/2017 | Sander et al. |
| 2017/0035428 A1 | 2/2017 | Binmoeller et al. |
| 2017/0354404 A1 | 12/2017 | Chu |
| 2018/0185183 A1 | 7/2018 | Christakis et al. |
| 2018/0193175 A1* | 7/2018 | Bluecher .................. A61F 2/90 |
| 2018/0263797 A1 | 9/2018 | Eller et al. |
| 2018/0303594 A1 | 10/2018 | Eller et al. |
| 2019/0099589 A1 | 4/2019 | Walsh et al. |
| 2019/0254804 A1 | 8/2019 | Folan et al. |
| 2020/0375768 A1 | 12/2020 | Eller et al. |
| 2021/0121306 A1 | 4/2021 | Henchie et al. |
| 2021/0145563 A1 | 5/2021 | Folan |
| 2021/0161692 A1 | 6/2021 | Mower et al. |
| 2022/0023026 A1 | 1/2022 | Eller et al. |
| 2023/0381000 A1 | 11/2023 | Eller et al. |

FOREIGN PATENT DOCUMENTS

| | | |
|---|---|---|
| DE | 102005051469 | 4/2007 |
| EP | 0364420 | 4/1990 |
| EP | 0408245 | 1/1991 |
| EP | 0872220 | 10/1998 |
| EP | 1637092 | 3/2006 |
| EP | 2522316 | 11/2012 |
| WO | 199631174 | 10/1996 |
| WO | 200018330 | 4/2000 |
| WO | 2000078246 | 12/2000 |
| WO | 2002056798 | 7/2002 |
| WO | 2002087470 | 11/2002 |
| WO | 2003090644 | 11/2003 |
| WO | 2004030571 | 4/2004 |
| WO | 2005070095 | 8/2005 |
| WO | 2008042266 | 4/2008 |
| WO | 2010130297 | 11/2010 |
| WO | 2013045262 | 4/2013 |
| WO | 2013052528 | 4/2013 |
| WO | 2013066883 | 10/2013 |
| WO | 2015184154 | 12/2015 |
| WO | 2019099080 | 5/2019 |
| WO | 2020146261 | 7/2020 |

OTHER PUBLICATIONS

Office Action dated Jan. 3, 2014 for U.S. Appl. No. 11/432,964.
Office Action dated Jul. 25, 2013 for U.S. Appl. No. 11/432,964.
Office Action dated Aug. 13, 2012 for U.S. Appl. No. 10/585,430.
Office Action dated Sep. 19, 2018 for U.S. Appl. No. 15/061,107.
Office Action dated Oct. 7, 2015 for U.S. Appl. No. 13/664,234.
Office Action dated Oct. 16, 2015 for U.S. Appl. No. 13/664,267.
Office Action dated Oct. 16, 2017 for U.S. Appl. No. 15/061,107.
Office Action dated Nov. 9, 2010 for U.S. Appl. No. 10/585,430.
Office Action dated Nov. 14, 2012 for U.S. Appl. No. 12/535,980.
Office Action dated Nov. 14, 2018 for U.S. Appl. No. 15/263,741.
Office Action dated Nov. 19, 2015 for U.S. Appl. No. 13/664,137.
Office Action dated Nov. 30, 2016 for U.S. Appl. No. 13/664,137.
Office Action dated Dec. 2, 2019 for U.S. Appl. No. 15/718,419.
Office Action dated Dec. 7, 2009 for U.S. Appl. No. 11/432,964.
Office Action dated Dec. 8, 2009 for U.S. Appl. No. 10/585,430.
Office Action dated Dec. 22, 2020 for U.S. Appl. No. 15/921,220.
Cheon, et al.,Clinical Feasibility of a New Through-The-Scope Fully Covered Esophageal Self-Expandable Metallic Stent: An In Vivo Animal Study, Digestive Endoscopy, vol. 26 No. 1 ,2014 ,32-36.
Kawakami, et al.,Endoscopic Ultrasound-Guided Transluminal Drainage for Peripancreatic Fluid Collections: Where are we now?, Gut and Liver, vol. 8 No. 4 ,2014 ,341-355.
Sen, et al.,Laplace's Equation for Convective Scalar Transport in Potential Flow, Proc. R. Soc. Lond. A 456, pp. 3041-3045 ,2000.
Sizarov, et al.,Novel materials and Devices in the Transcatheter Creation of vascular Anastomosis—The Future Comes Slowly (Part 2), Archives of Cardiovascular Diseases, vol. 109 No. 4 ,2016 ,286-295.
Weilert, et al.,Specially Designed Stents for Translumenal Drainage, Gastrointestinal Intervention, vol. 4 No. 1 ,2015 ,40-45.
European Search Report dated Nov. 9, 2020 for EP18767753.9.
International Search Report and Written Opinion dated Feb. 14, 2022 for PCT/US2021/056495.
International Search Report and Written Opinion dated Nov. 9, 2021 for PCT/US2021/042833.
Notice of Allowance dated Jul. 22, 2020 for U.S. Appl. No. 15/718,419.
Office Action dated Apr. 15, 2022 for U.S. Appl. No. 15/921,220.
Office Action dated Nov. 9, 2021 for U.S. Appl. No. 15/921,220.
Office Action dated Nov. 25, 2022 for U.S. Appl. No. 16/994,260.
European Examination Report dated Feb. 18, 2015 for EP09791142.4.
European Examination Report dated Apr. 26, 2021 for EP11846358.7.
European Search Report dated Mar. 19, 2021 for EP18768455.0.
European Search Report dated Apr. 24, 2020 for EP17857414.1.
European Search Report dated Dec. 15, 2020 for EP18768455.0.
European Search dated Sep. 24, 2018 for EP16759580.
International Preliminary Report dated May 15, 2014 for PCT/US2012/062603.
International Publication and Search Report dated Jun. 14, 2012 for WO2012078794.
International Publication and Search Report dated Feb. 25, 2012 for WO2010021836.
International Search Report and Written Opinion dated Mar. 16, 2012 for PCT/US2011/063799.

(56) References Cited

OTHER PUBLICATIONS

International Search Report and Written Opinion dated Mar. 29, 2013 for PCT/US2012/062603.
International Search Report and Written Opinion dated Jun. 22, 2016 for PCT/US2016/020900.
International Search Report and Written Opinion dated Jun. 29, 2018 for PCT/US2018/022340.
International Search Report and Written Opinion dated Jun. 29, 2018 for PCT/US2018/022344.
International Search Report and Written Opinion dated Aug. 2, 2018 for PCT/US2018/028107.
International Search Report and Written Opinion dated Sep. 28, 2005 for PCT/US2005/000515.
International Search Report and Written Opinion dated Oct. 29, 2009 for PCT/US2009/052691.
International Search Report and Written Opinion dated Nov. 23, 2006 for PCT/US2006/018811.
Notice of Allowance dated Jan. 14, 2015 for U.S. Appl. No. 11/432,964.
Notice of Allowance dated Feb. 25, 2019 for U.S. Appl. No. 15/061,107.
Notice of Allowance dated Mar. 6, 2013 for U.S. Appl. No. 12/535,980.
Notice of Allowance dated Jun. 11, 2013 for U.S. Appl. No. 10/585,430.
Notice of Allowance dated Jun. 22, 2016 for U.S. Appl. No. 13/664,267.
Notice of Allowance dated Aug. 12, 2015 for U.S. Appl. No. 13/664,200.
Notice of Allowance dated Sep. 6, 2018 for U.S. Appl. No. 29/597,873.
Notice of Allowance dated Sep. 11, 2019 for U.S. Appl. No. 15/263,741.
Notice of Allowance dated Sep. 23, 2016 for U.S. Appl. No. 13/664,234.
Notice of Allowance dated Oct. 21, 2014 for U.S. Appl. No. 13/313,929.
Office Action dated Jan. 22, 2013 for U.S. Appl. No. 10/585,430.
Office Action dated Jan. 31, 2012 for U.S. Appl. No. 10/585,430.
Office Action dated Feb. 5, 2020 for U.S. Appl. No. 15/921,172.
Office Action dated Mar. 6, 2020 for U.S. Appl. No. 15/955,895.
Office Action dated Mar. 16, 2015 for U.S. Appl. No. 13/664,234.
Office Action dated Mar. 22, 2016 for U.S. Appl. No. 13/664,234.
Office Action dated Mar. 24, 2015 for U.S. Appl. No. 13/664,267.
Office Action dated Apr. 6, 2016 for U.S. Appl. No. 13/664,137.
Office Action dated Apr. 7, 2020 for U.S. Appl. No. 15/955,895.
Office Action dated Apr. 25, 2018 for U.S. Appl. No. 15/061,107.
Office Action dated May 5, 2014 for U.S. Appl. No. 13/313,929.
Office Action dated May 21, 2021 for U.S. Appl. No. 15/921,220.
Office Action dated May 25, 2012 for U.S. Appl. No. 12/535,980.
Office Action dated May 30, 2019 for U.S. Appl. No. 15/263,741.
Office Action dated Jun. 7, 2011 for U.S. Appl. No. 10/585,430.
Office Action dated Jul. 9, 2009 for U.S. Appl. No. 11/432,964.
Notice of Allowance dated Mar. 15, 2023 for U.S. Appl. No. 16/994,260.
International Publication and Search Report dated Aug. 4, 2005 for WO2005070095.
Office Action dated Oct. 26, 2023 for U.S. Appl. No. 17/383,221.

* cited by examiner

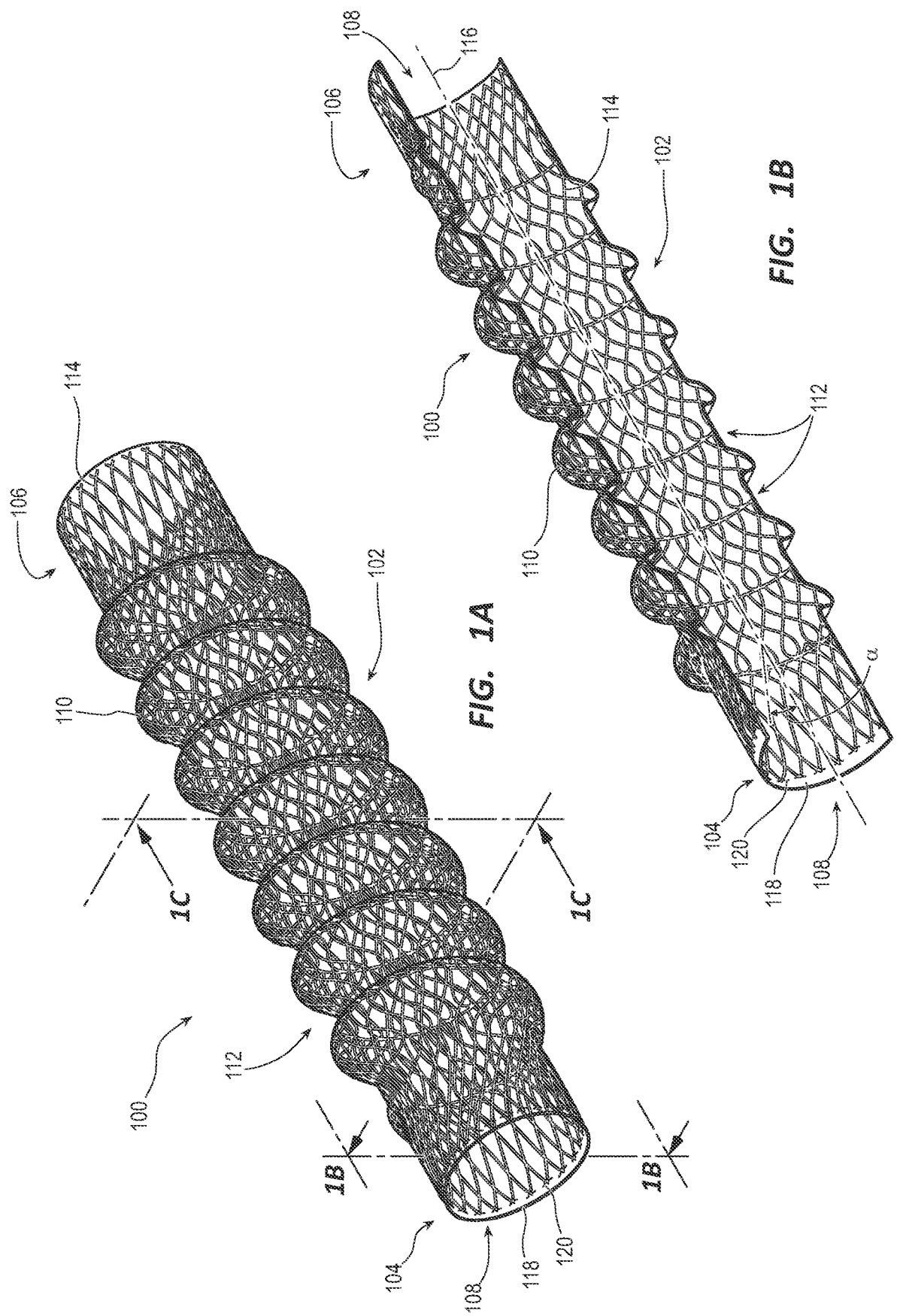

ESOPHAGEAL STENTS WITH HELICAL THREAD

RELATED APPLICATIONS

This application claims priority to U.S. Provisional Patent Application No. 63/105,747, filed on Oct. 26, 2020, entitled "ESOPHAGEAL STENTS WITH HELICAL THREAD," which is hereby incorporated herein by reference in its entirety.

TECHNICAL FIELD

This application generally relates to medical devices. More particularly, this application relates to stents having particular structural features.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 1A is a perspective view of a stent in accordance with an embodiment.

FIG. 1B is a cross-sectional view of the stent shown in FIG. 1A taken on the plane indicated in FIG. 1A as 1B.

DETAILED DESCRIPTION

Figure 1C:
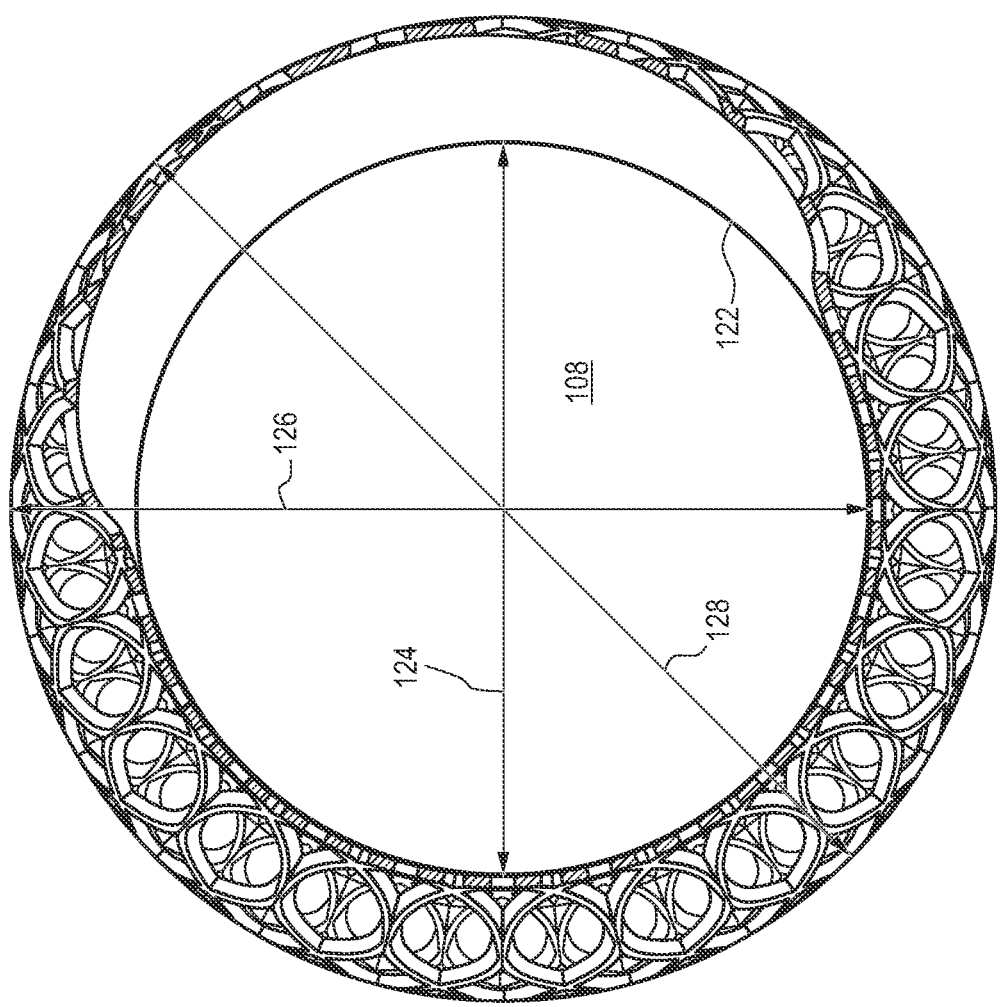
FIG. 1C is a cross-sectional view of the stent shown in FIG. 1A taken on the plane indicated in FIG. 1A as 1C.

Stents are disclosed herein. In some embodiments, the stents described herein comprise a tubular body having an interior dimension and comprising a midbody that extends to a first end and also extends to an opposing second end, where the midbody includes a thread arranged helically along at least a portion of its length. The thread can exhibit various shapes and/or dimensions selected to enhance particular aspects of performance when the stent is placed in an anatomical structure of a patient. Though stents may be described herein with reference to placement in the esophagus, this should be understood as one exemplary use. Stents in accordance with the present disclosure can be used in a number of placements, including but not limited to, gastrointestinal, colonic, biliary, pulmonary, vascular, pancreatic, and ureteral placements.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrase "coupled to" refers to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As applied to a stent deployed within an esophagus, the proximal end of the stent refers to the end closest to the patient's head, and the distal end of the stent refers to the opposite end, the end closer to the patient's stomach.

FIG. 1A and FIG. 1B depict a stent 100 having a generally tubular structure that comprises a midbody 102 extending to two opposing ends, i.e., a first end 104 and a second end 106, which combine to define a lumen or an interior space 108 passing through the stent 100. The first end 104 and second end 106 can respectively be considered the proximal end and the distal end of the stent for purposes of the descriptions herein, unless expressly stated otherwise. The stent 100 includes a helical thread 110 arranged circumferentially along a portion of the outer surface of at least the midbody 102 of the stent 100. In some embodiments as illustrated in FIG. 1A and FIG. 1B, the midbody 102 comprises a helical thread 110 and interthread spaces 112, which together define the portion of the interior space 108 between the ends 104, 106 of the stent 100.

As illustrated in FIG. 1B, which presents a cross-sectional view taken at the plane "1B" shown in FIG. 1A, the helical thread 110 can be formed as an outward expansion of the structure of the stent 100, such that the helical thread 110 protrudes radially from the portion of the stent 100 on which it is located (e.g., the midbody 102). Therefore, in an aspect of the present disclosure, the helical thread 110 can constitute a primary contact surface between the stent 100 and the surrounding tissue of a body lumen in which it is placed, whereby the helical thread 110 allows the stent 100 to grip the tissue more effectively. This grip aids in anchoring the stent, therefore the helical thread 110 can enhance the stent's 100 resistance to migration within the lumen. While not bound by any particular theory, due to its helical arrangement, the helical feature can function somewhat as a screw thread in the classical sense, i.e., providing conversion between longitudinal motion and rotational motion. More specifically, forces acting on the stent 100 that would tend to produce longitudinal migration are instead translated into rotational forces, thereby greatly reducing longitudinal displacement of the stent 100.

In another aspect, the inclusion of helical threads 110 may also aid in fluid flow through stented regions. For example, spiral laminar flow is a predominant type of arterial flow and is commonly seen in narrowing passages in the circulatory system. While not bound by any particular theory, the helical arrangement of the threads 110 can facilitate or enhance such flow in certain anatomical structures.

In other aspects, the helical thread 110 can enhance the mechanical properties of the stent 100. In one aspect, the helical thread 110 increases the axial and radial strength of the stent 100. This can be realized to a greater degree as stent 100 length increases, as compared to conventional unthreaded stents in which radial and axial strength decrease more drastically with increasing length. In another aspect, the helical thread 110 can decrease the stent's 100 resistance to lateral flexion, i.e., its bending force. Stated differently, the turns of the helical thread 110 provide flexion points that allow the stent 100 to bend more easily. The helical thread also enables the stent body to remain more open when placed in narrowing and tortuous anatomy, resisting collapsing/infolding. This can make the stent 100 more suited for navigating small and/or tortuous anatomy while keeping the lumen open and exerting less pressure on said anatomy.

In various embodiments, the stent 100 may comprise any suitable material known in the art, including metals, alloys thereof, and polymers. In some embodiments, the material may be a memory alloy, including but not limited to an alloy of nickel and titanium commonly known as Nitinol. In one example, biliary stents are made using "DFT wire" (drawn filled tubing) which consists of a Nitinol outer sheath and a core containing platinum to give fluoroscopic visibility. Other metals include magnesium, zinc, and iron. In some embodiments, the stent 100 can comprise a biodegradable material.

In some embodiments the stent 100 can comprise a grid or mesh structure. As illustrated in FIG. 1A, the mesh structure can be formed of wire 114 braided or woven according to a pattern. More specifically, the wire 114 can be arranged in a particular braid pattern having a pitch, and with a braid angle α that can be constant over a given region of the stent 100 and also vary over other regions to provide certain shape and strength characteristics. The pattern comprises repeating structural units, the most basic of which being cells, which are the openings formed by sets of adjacent crossing points of the wire 114.

In some embodiments, the braid pattern of the midbody (and/or of the entire stent) is a one-wire, two-over, two-under braid pattern (referred to as a "one over two" pattern), which means that a single strand passes over two strands (or two different portions of itself, such as in a single wire braid design) and then under two other strands (or yet two other portions of itself, such as in a single wire braid design). Alternative braid patterns may be used as well, such as a one-wire, one-over, one-under braid pattern (referred to as a "one over one" pattern). Other possible braid patterns include the diamond two-wire, one-over, one-under braid pattern and the diamond two-over, two-under braid pattern. Two strands can also be 'hooked,' or linked, together at their crossing point rather than passing over/under one another uninterrupted.

In some embodiments, the braid pattern may lead to differing cell requirements over the length of the stent 100, where a cell refers to the design created by the braid pattern. Thus, depending on stent length and braid pattern, the braid designs may result in fractional and non-fractional cell counts. For example, a stent 100 may be designed with a non-fractional cell count, in which a full braid pattern is completed on each end of the stent 100 and/or the stent 100 comprises only full braid patterns along the length of the stent 100. Non-fractional cell counts refer to a whole cell count. For example, a stent 100 with a non-fractional cell count may have, 20, 30, 40, 50, or more full cell counts, or full braid patterns along its length. Fractional cell counts refer to fractional cell count numbers, 20.5, 30.5, 40.5, 50.5 or more, meaning the stent 100 has a whole number of full cell counts in addition to a partial cell (or braid pattern) along the length of the stent 100. In some embodiments, the braid pattern may be one over one and may have a fractional or non-fractional cell count. In some embodiments, the braid pattern may be one over two and may have a fractional or non-fractional cell count.

As shown in FIG. 1B, the braid angle α is an angle formed by a given strand of the braided or woven wire 114 relative to the longitudinal axis 116 of the stent 100. A larger (higher) braid angle, approaching, for example, 90 degrees, results in a higher pic count (number of points of intersection of the strands) per given longitudinal length (e.g., an inch) of a given braid (or weave) pattern. These parameters can be varied to impart certain characteristics to the stent body. A higher pic count can produce greater stiffness (i.e., a lower degree of compressibility). A smaller (lower) braid angle results in a lower pic count per given longitudinal length, which can result in greater softness (i.e., less stiffness and a higher degree of compressibility). In some embodiments, the braid angle α is from about 35 degrees to about 90 degrees. In certain of such embodiments, the braid angle α in the interthread spaces 112 is from about 40 degrees to about 60 degrees, and the braid angle α on the helical thread 110 is from about 50 degrees to about 80 degrees. In an aspect, the braid angle α on the thread 110 can vary based on thread height/geometry and starting angle from midbody 102.

The pitch (i.e., axial distance between intersecting strands) also impacts the compressibility and stiffness of the braided or woven wires 114. In an aspect, a decrease in pitch, i.e. tighter pitch, may correlate with an increase in migration resistance of the stent 100. The pitch is related to the number of strands woven or braided together and the braid angle α, and therefore can vary over different geometries.

The braided or woven wires 114 may be braided or woven in a given pattern in accordance with an appropriate braid design, such as a closed-loop braid design, a single wire woven design, an endless braid design, or the like. In some embodiments, the wire 114 is braided in a closed-loop braid design in which multiple strands are interlaced in a first direction (e.g., a distal direction) and then turn and are interlaced back in an opposite second direction (e.g., back in the proximal direction). In still other embodiments, the stent 100 may have an endless braid design in which multiple strands are interlaced. In some embodiments, the braid pattern can comprise hook stitches. In other embodiments, a "hook and cross" braid pattern is used in which the pattern includes both hook stitches and cross stitches. In some embodiments, the braid pattern is created using an axial braiding approach. In some embodiments, the braid pattern is created using a radial braiding approach. Radial braiding involves creating a fractional cell count along the length of the stent, either a non-fractional or a fractional cell count can be selected with axial braiding.

In various embodiments, the braided or woven wires 114 are braided or woven so as to create a series of loops at one or both ends of the stent 100. The arrangement of these loops can be selected to provide desired functionality, such as for threading through of a suture line (discussed further below). In some embodiments the end loops are substantially aligned in one plane at the stent opening. In other embodiments, some end loops may protrude further than others. In certain embodiments, the length of the end loops can alternate.

The braided or woven wires 114 may include varying numbers of strands, where the number used can depend in part upon the size of the stent 100 and the braid or weave pattern. In some embodiments, the stent 100 includes a wire count from 24 to 72 wires, or more particularly from 32 to 64 wires, or more particularly from 48 to 56 wires. In other embodiments, a biliary stent in accordance with the present disclosure has a wire count from 16 to 44 wires. Wire counts increase by a factor of 4 with 1-over-1 braid patterns and by a factor of 8 with 1-over-2 braid patterns.

When braided or woven in a closed-loop braid design, the braided or woven wires 114 may start and stop at various locations on the stent 100. In an aspect, it can be advantageous to design the braid so that such termination points occur on surfaces of a substantially flat/uniform cylindrical geometry.

In certain embodiments, the thickness of a strand of the braided or woven wires 114 may be about 102 μm to about 381 μm, or more particularly from 140 μm to about 254 μm. In other embodiments, the thickness may be about 165 μm to about 178 μm. Generally speaking, smaller wires may be used with smaller diameter stents and larger diameter wires may be used with larger diameter stents. Also, while smaller diameter wires can be used for stents designed for "through the scope" placement, stents designed for "over the wire" placement can include wires having significantly larger diameters. Radiopaque markers and/or coils can also be incorporated into the stent 100 as desired.

In certain embodiments, the grid or mesh structure can be formed from a tube of a suitable material where the pattern is created by cutting material from the tube using a laser. In the case of a stent made from polymeric materials, the stent could be fabricated using 3D printing.

In some embodiments, as illustrated in FIG. 1A and FIG. 1B, the stent 100 may be coated or covered along its entire length or over portions thereof with a cover 118. The cover 118 can comprise a flexible material suitable for placement in a body lumen, such as polyurethane or silicone. The cover is coupled to the braided or woven wire 114 or other material that forms the body of the stent 100. The cover 118 can further define the interior space 108 of the stent 100 and can facilitate passage of particles or fluid through the lumen of the stent 100.

The cover 118 may be elastomeric, polymeric, or comprised of any other material suited/approved for use in the body. In some embodiments, the cover 118 may include polyurethane or silicone. In some embodiments, the cover may be applied such that it tends to ebb and flow into spaces between portions of the braided or woven wires 114, resulting in a "tire tread" like outer surface, rather than a smooth outer cover 118. This can allow tissue to lock into the pockets of the outer surface, thus potentially adding to the anti-migration properties in some embodiments. In some embodiments, the cover 118 is shaped such that the braided or woven wires 114 are uncovered in some regions of the stent 100, which can allow tissue to grow into these spaces to help secure the stent 100 in place. In some embodiments, the cover 118 can comprise two or more layers of material.

In addition, the stent 100 can include a suture 120 arranged about the proximal and/or distal ends of the stent 100. In some embodiments, the suture 120 can be woven through end loops formed at the end of the stent 100. The suture 120 can be configured to aid with loading of the stent 100 into a catheter or other delivery device and can also facilitate removal of the stent 100 from the body of a subject. The suture 120 may be woven in such a way that pulling it has a drawstring effect on the opening of the end of the stent 100. That is, pulling a portion of the suture 120 causes the suture 120 to draw the edges of the stent ends 104 and 106 and the cover 118 radially inward, elongating and narrowing the stent 100. In the case where the stent 100 is situated in a body lumen, this action facilitates removal by aiding disengagement of the stent 100 from the lumen wall.

FIG. 1C presents another cross-sectional view, in this case taken at the plane labeled "1C" in FIG. 1A. In various embodiments, as illustrated in FIG. 1C, the interthread spaces 112 of the midbody define a generally cylindrical profile 122 having a profile diameter 124 from which the helical thread 110 protrudes radially. The outermost peak of the helical thread 110 protrudes from the profile 122 at a height such that the thread extends the profile diameter 124 to a peak diameter 126. In an aspect, the peak diameter 126 corresponds to the maximum diameter of the interior space 108 at any point along the midbody 102 where the thread is present. The height of the helical thread 110 in absolute terms can be selected in part based on the dimensions—e.g., length, diameter—of the stent 100, as well as on aspects of the anatomical structure into which the stent 100 will be placed. In certain embodiments, the height of the helical thread 110 is from about 0.5 mm to about 5 mm, or from about 1 mm to about 4 mm, or from about 2 mm to about 3 mm. In some embodiments, in relative terms the height of the helical thread 110 is from about 2.5% to about 30% of the profile diameter, such that the peak diameter 126 (i.e., the profile diameter plus the height of one instance of the thread) is from about 2.5% to about 30% greater than the profile diameter 124. In certain embodiments, the peak diameter 126 is from about 5% to about 25% greater than the profile diameter 124. Accordingly, a full turn of the helical thread 110 defines an overall diameter 128 of the midbody 102 that is from about 5% to about 60% or from about 10% to about 50% greater than the profile diameter 124.

In an aspect of the present disclosure, the features described herein provide for a wider array of stent dimensions. In some embodiments, the overall length of the stent may range from about 20 mm to about 250 mm, including ranging from about 20 mm to about 90 mm, or from about 60 mm to about 160 mm. In particular examples, the stent can have an overall length of about 100 mm and the midbody can have a length of about 50 mm, an overall length of about 120 mm and a midbody length of about 70 mm, or an overall length of about 150 mm and a midbody length of about 100 mm. The overall diameter can be from about 6 mm to about 45 mm. In particular embodiments, the overall diameter is about 6 mm to about 30 mm, or from about 14 mm to about 30 mm, or from about 30 mm to about 45 mm.

Figure 2:
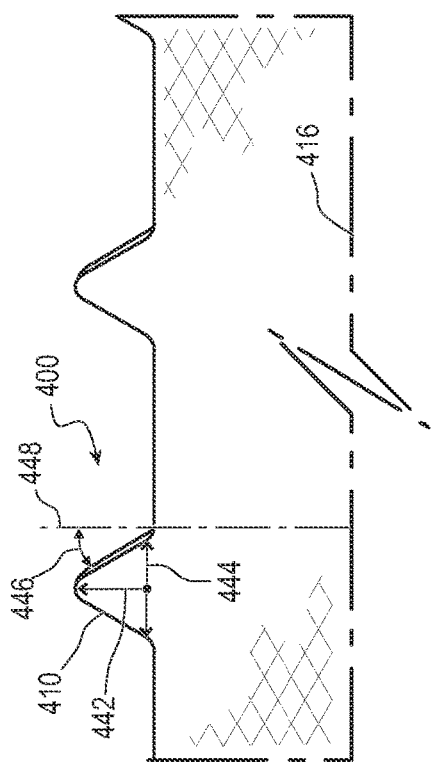
FIG. 2 is a longitudinal cross-section of a portion of a stent in accordance with an embodiment.

The helical thread can have a cross-sectional shape, which may be selected with a view to enhancing migration resistance in a particular anatomical structure and/or based on consideration of the materials and method used to fabricate the stent. In some embodiments, the helical thread can have a generally circular cross-sectional profile—i.e., the shape of the thread's profile defines at least part of a circle. FIG. 2 shows a longitudinal cross-section of a portion of an exemplary stent 200 having helical thread 210 with a generally circular profile. As illustrated in FIG. 2, the shape of the thread's profile defines a part of a circle 230 having a diameter 232 which also defines the maximum breadth of the helical thread 210. The radius 234 of the circle 230 defines the height of the thread 210. In some embodiments, the diameter 232 is from about 1 mm to about 10 mm. In embodiments in which the thread has a semicircular profile such as the exemplary stent 200 in FIG. 2, the radius 234 determines the maximum height of the thread 210, which will be about one-half the maximum width of the thread 210.

Figure 3:
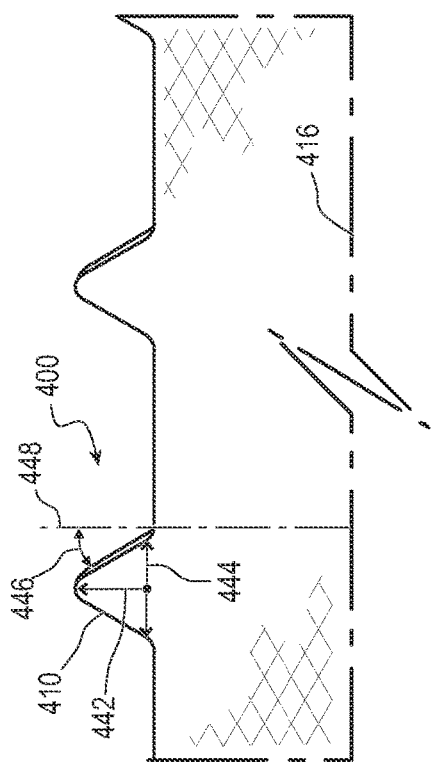
FIG. 3 is a longitudinal cross-section of a portion of a stent in accordance with another embodiment.

In some embodiments, the helical thread can have a cross-sectional profile with a generally elliptical geometry. FIG. 3 shows a longitudinal cross-section of a portion of an exemplary stent 300 where the helical thread 310 has cross-sectional profile that defines a part of an ellipse 336 having a minor diameter 338 and major radius 340 based respectively on its minor and major axes. In an aspect of the embodiment, the minor diameter 338 defines the maximum breadth of the helical thread 310. In some embodiments, the minor diameter 338 is from about 0.5 mm to about 10 mm. In another aspect, the major radius 340 defines the height of the helical thread 310. In certain embodiments such as exemplified in FIG. 3, the major radius 340 represents the maximum height of the helical thread 310. In some of such embodiments, the major radius 340 is from about 0.5 mm to about 5 mm.

Figure 4:
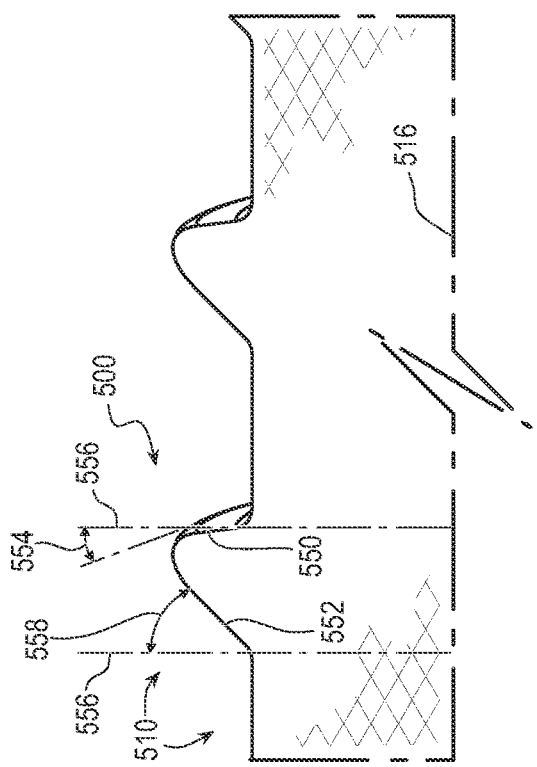
FIG. 4 is a longitudinal cross-section of a portion of a stent in accordance with another embodiment.

In various embodiments, the helical thread has a generally triangular cross-sectional profile. In some embodiments, an example of which is shown in FIG. 4, a stent 400 includes a helical thread 410 having a cross-sectional profile with a roughly symmetrical inverted "V" shape. In an aspect, this shape substantially defines an isosceles triangle having a height 442 and a base width 444, which correspond respectively to the height and breadth of the helical thread 410. In another aspect, this shape may provide faces that exhibit particular angles, such as an exterior angle 446 from perpendicular 448 to the longitudinal axis 416. In particular embodiments, the exterior angle 446 can be from about 10 degrees to about 35 degrees (with the peak having a corresponding interior angle of from about 20 degrees to about 70 degrees). In some of such embodiments, the height 442 of the helical thread 410 is from about 1 mm to about 5 mm.

Figure 5:
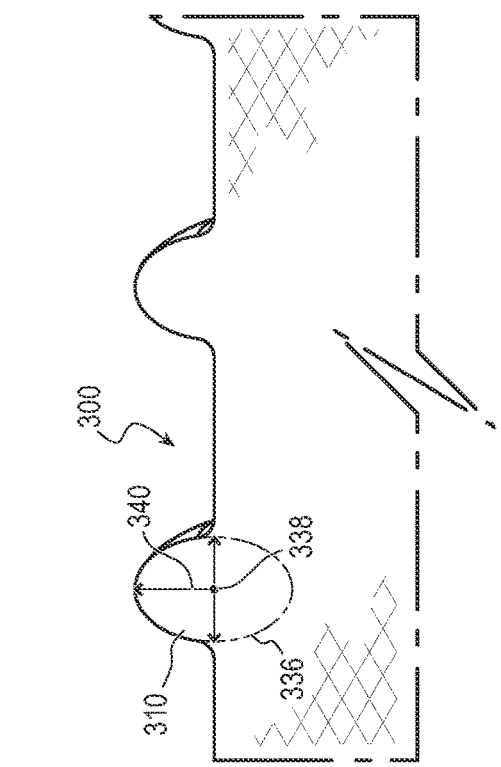
FIG. 5 is a longitudinal cross-section of a portion of a stent in accordance with another embodiment.

In some embodiments, the helical thread has a buttress-shaped cross-sectional profile, one example embodiment of which is shown in FIG. 5. As shown, a stent 500 can comprise a helical thread 510 having a cross-sectional profile with a buttress shape in which the faces of the thread differ in their respective angle. More particularly, the shape can include a thrust face 550 and a bracing face 552, wherein the thrust face 550 is oriented at a first angle 554 from perpendicular 556 to the longitudinal axis 516 that is less than a second angle 558 of the bracing face 552 from the perpendicular 556. In particular embodiments, the first angle 554 can be from about 5 degrees to about 20 degrees and the second angle 558 from about 30 degrees to about 60 degrees. In some of such embodiments, the height of the helical thread 510 is from about 1 mm to about 5 mm.

Without being bound by or limited to a particular theory, such a shape may enhance migration resistance, where the thrust face 550 of the thread exerts force against the surrounding tissue to resist movement of the stent 500 in a particular direction, while the bracing face 552 performs a bracing function to strengthen and support the thrust face 550. Accordingly, in some embodiments, the helical thread 510 can be shaped such that the thrust face 550 faces the end of the stent 500 oriented in the direction in which migration is least desirable. For example, the thrust face 550 can face the distal end of a stent for use in an application (e.g., stenting of the esophagus) in which migration in the distal direction is more common.

The cross-sectional profile shapes described above are not intended to be exhaustive, and it is contemplated that stents in accordance with the present disclosure may include threads having other cross-sectional shapes as well as combinations of the foregoing. With respect to the various cross-sectional profile shapes, the height and breadth of the helical thread in absolute terms may depend to a degree on the overall dimensions of the stent, and the relationship between the height and breadth is determined in part by the profile geometry. For example, in some embodiments a stent (e.g. an esophageal stent) comprises a helical thread with a profile based on a circle having a diameter of from about 1 mm to about 10 mm, such that the maximum height of the helical thread is from about 0.5 mm to about 5 mm and the maximum width of the helical thread is from about 1 mm to about 10 mm. Some embodiments of a stent (e.g. an esophageal stent) can comprise a helical thread with a profile based on an oval having major diameter from about 1 mm to about 10 mm, such that the maximum height of the helical thread is from about 0.5 mm to about 5 mm and maximum width is from about 0.5 mm to 10 mm.

In various embodiments, a stent can comprise a helical thread having a plurality of thread heights. In some embodiments, the height of the thread can vary along a length of the stent, e.g., generally increasing or generally decreasing in height from one end to the other or varying in heights from one end to the other. In another example, the stent comprises two or more such helical threads or regions thereof exhibiting increasing height, decreasing height, or a combination thereof.

A particular aspect of the various embodiments discussed herein is the spacing between adjacent turns of the helical thread. The thread spacing (also termed "pitch") can be selected with a view to providing desired benefits and performance in particular stenting applications. In one aspect, as discussed above, the helical thread contributes to the axial strength of the stent. The degree to which the thread enhances axial strength is affected by the thread spacing, where decreased thread spacing increases axial strength. One manifestation of increased axial strength is increased resistance to stretching. Accordingly, in various embodiments the thread spacing is selected so as to be small enough to provide a useful degree of axial strength, while not being so small as to produce a degree of spring-like behavior that may increase migration of the stent. For example, some decrease in spacing can increase the self-expansion force, i.e., hoop force of the stent, which contributes to migration resistance by enhancing contact between the outer surface of the stent and surrounding tissue. In a related aspect, as each turn of the helical thread provides a contact surface that interacts with surrounding tissue, such a decrease in thread spacing will result in the stent exhibiting a higher thread density as well as more total turns of the thread, thereby increasing migration resistance. In another aspect of the foregoing, decreasing thread spacing beyond a certain point decreases the spacing and structure between the thread features, which may result in the loss or reversal of such effects, i.e., decreased hoop force and decreased flexibility resulting in decreased migration resistance. These respective spacing ranges may depend upon various design parameters including, but not limited to, the type of stent, the dimensions of the stent, wire count, and wire size.

Figure 6:
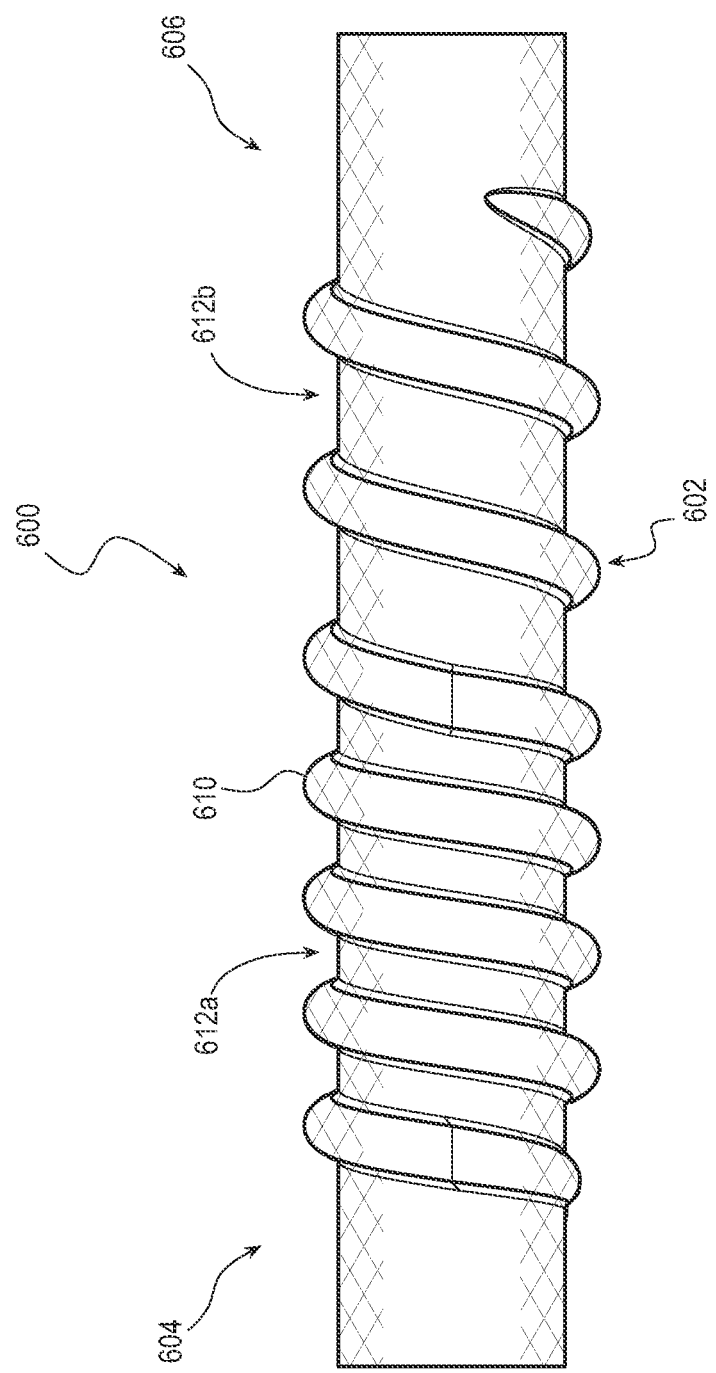
FIG. 6 is a side view of a stent in accordance with another embodiment.

In some embodiments, a stent can comprise a helical thread having a constant thread spacing. In other embodiments, a helical thread can include a plurality of thread spacings. FIG. 6 shows an illustrative embodiment in which a stent 600 comprises a first end 604, a second end 606, and a midbody 602, where the midbody includes a helical thread 610 which exhibits a tighter spacing near the first end 604 and a looser spacing near the second end 606. Stated differently, an interthread space 612a near the first end 604 is shorter in length than an interthread space 612b near the second end 606. In some embodiments, the helical thread can include two, three, four, or more discrete spacings. In other embodiments, the thread spacing can increase or decrease continuously from one end of the helical thread to the other. In other embodiments, the thread spacing can vary randomly among individual turns or groups of turns of the helical thread. In some embodiments, the thread spacing may vary based on the shape of the stent. For example, a stent with a conical midbody (e.g. lung stents) may include a helical thread in which thread spacing changes with the changing diameter of the midbody.

The actual spacing between turns of the helical thread in standard units of length can depend on the overall dimensions of the stent. In another aspect, thread spacing may be selected in view of the methods and materials used to fabricate the stent. For example, in stents constructed of woven or braided wire, thread spacing may be selected based on elements of the pattern. In a particular example, a thread spacing is selected so that the interthread space is at least from 1 to 7 cells in width, or more particularly from 2 to 5 cells in width. In certain embodiments, a stent can include interthread spaces from about 2 mm to about 20 mm, or more particularly from about 4 mm to about 15 mm. In more particular embodiments, the stent is constructed of braided wire and the interthread spaces are at least 2 cells in width.

In some embodiments, a stent may feature multiple regions in which the presence or absence of helical thread and/or the spacing of the helical thread is selected to accommodate the structure and function of the stent. For example, as discussed above, a stent may employ tighter spacing at regions along the stent where greater migration resistance and/or axial strength is desired, while exhibiting looser spacing (or alternatively, no thread at all) in other regions. In another example, increased thread spacing or absent threading may be employed in a region of a stent to accommodate design considerations associated with a specialized structure of that region (e.g., the presence of an anti-reflux valve in an esophageal stent so equipped).

In other embodiments, decreased thread pitch can be increased through the inclusion of more than one helical thread on a stent. For example, a stent can include two, three, or four helical threads, each of which starts at a different point around the circumference of the stent, either originating at the same or different positions along the axis of the stent. In a particular example, a stent can have a double start helical thread in which the two threads are positioned 180 degrees apart and start at the same position along the axis of the stent.

Figure 9:
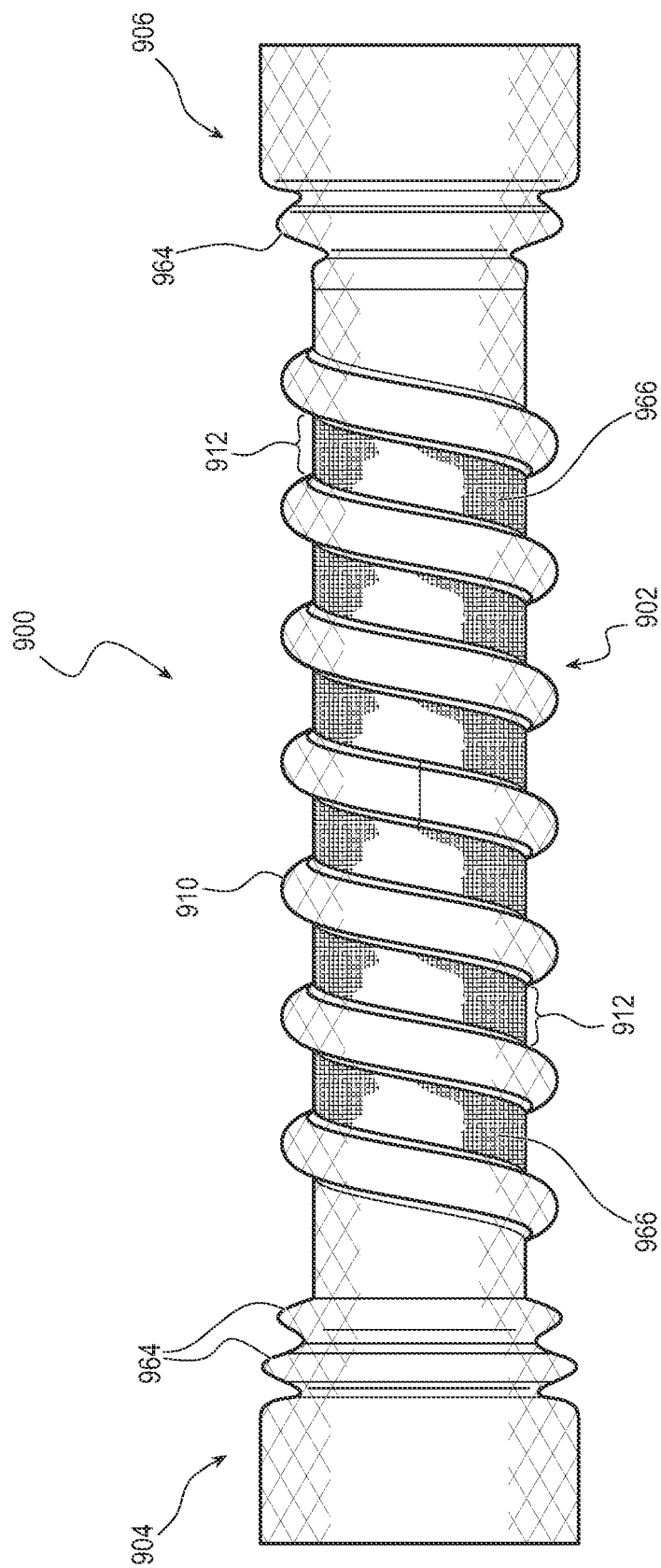
FIG. 9 is a side view of a stent in accordance with another embodiment.

Another aspect is the availability of the stent body or designated portions thereof, e.g., the interthread spaces or the thread itself, to include additional features, including but not limited to anti-migration features, adhesives, and the like. In some embodiments, as illustrated in FIG. 9 and discussed below, a specialized material can be situated over the entirety of the stent body, or in a designated portion thereof, such as in one or more interthread spaces. For instance, as shown in FIG. 9, the specialized material can be disposed as a strip that extends along the interthread spaces. In some of such embodiments, the width of the strip is from about 1 mm to about 12 mm, or more particularly from about 3 mm to about 6 mm. In some embodiments, the specialized material provides a textured surface. In certain embodiments, the textured surface produces increased and/or decreased friction with surfaces with which the stent comes into contact, e.g., a tissue surface. In a particular example, the textured surface includes a multilayered/micropatterned surface in which friction is dependent on conditions in its environment, for example the wetness of the contacting surface, e.g. tissue, and the surrounding environment. Examples of such micro-textured materials are described in U.S. Patent Application Publication Nos. 2011/0311764 and 2017/0014111. In an aspect, such material can provide the stent with enhanced grip on surrounding tissues with less injury to said tissues. Another aspect of the inclusion of specialized material in the interthread space of stents of the present disclosure is that the protruding adjacent helical thread can protect the material from undesirable contact in some contexts. For example, the thread can provide such protection during loading into the deployment device and subsequent navigation through the anatomy and placement of a stent using both "through the scope" and "over the wire" methods.

Figure 7:
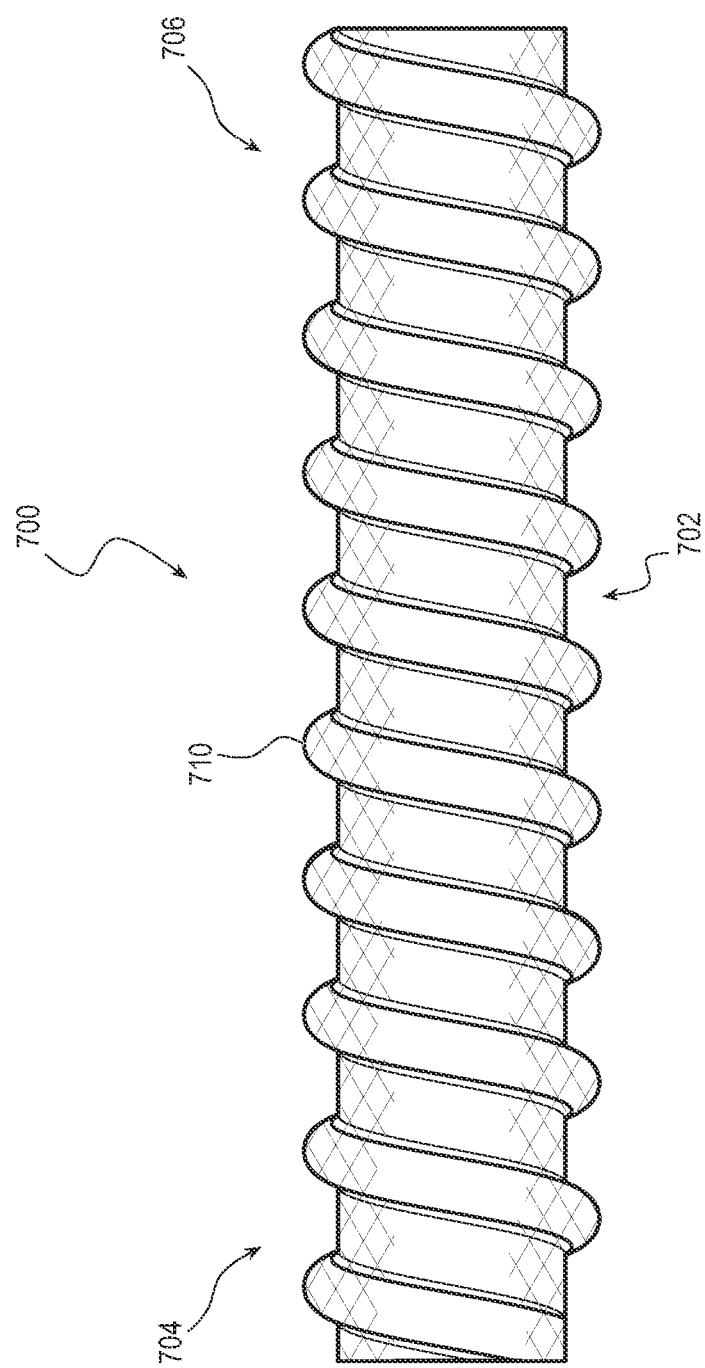
FIG. 7 is a side view of a stent in accordance with another embodiment.

Similarly, in some embodiments a helical thread may be included in areas of the stent in addition to the midbody. In some embodiments, a helical thread can be employed on one or both ends of a stent, either in addition to helical threads on the stent midbody or exclusively, i.e., without thread features on the stent midbody. As illustrated in FIG. 7, a stent 700 can comprise a first end 704, a second end 706, and a midbody 702. The stent 700 further comprises a helical thread 710 that is present not only on the midbody 702 but also on at least part of the first end 704 and second end 706.

Figure 8:
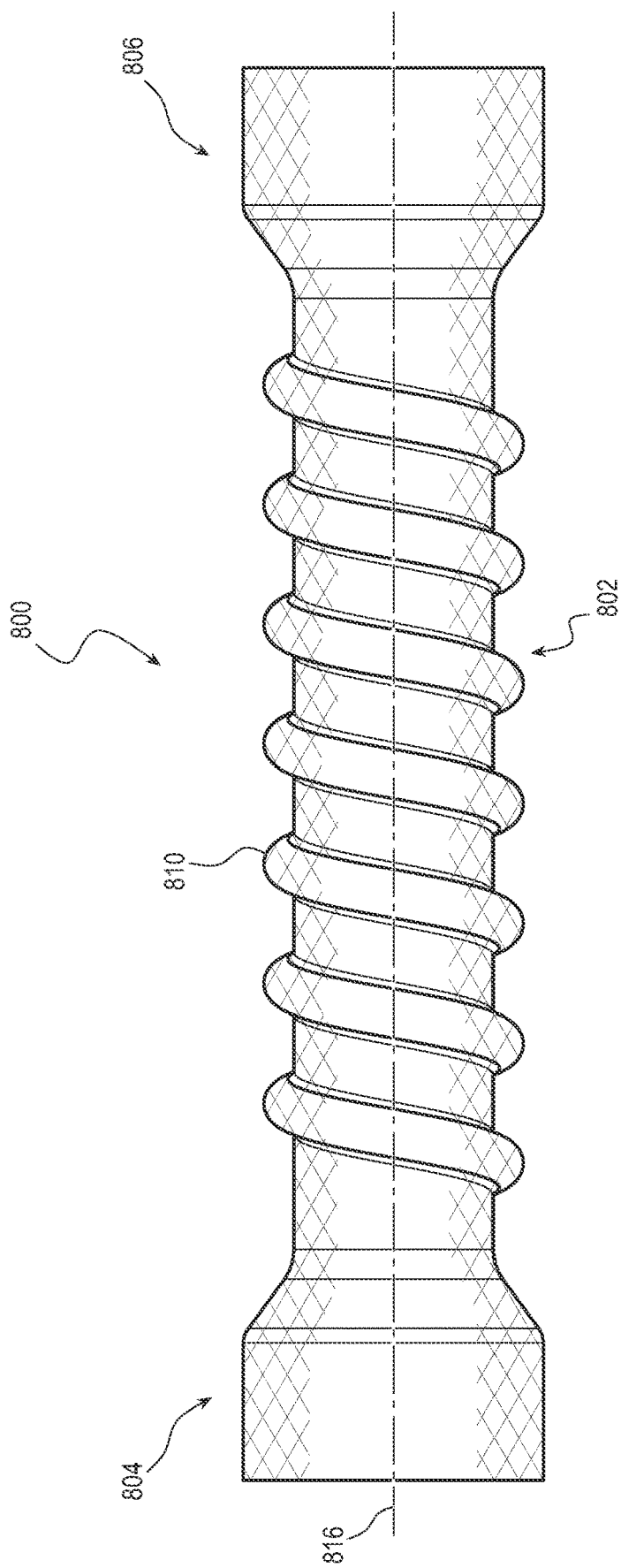
FIG. 8 is a side view of a stent in accordance with another embodiment.

Stents with helical threads in accordance with the present disclosure can also include other structural features. FIG. 8 shows a stent 800 having a midbody 802 with a helical thread 810, and a first flange 804 and a second flange 806, wherein the first flange 804 and second flange 806 flare to a diameter greater than the overall diameter of the midbody 802. In certain embodiments, as exemplified by FIG. 8, the flanges each have a cylindrical shape that is concentric to the axis 816 of the stent 800. In other embodiments, one or both flanges can have a conical shape. In still other embodiments, one or both flanges can taper back toward the axis 816 of the stent 800.

In an aspect of the foregoing, the flanges may contribute to migration resistance by interacting with the surfaces of a lumen in a subject's body. In some embodiments, additional anti-migration benefits may be realized by increasing the number of flanges to provide additional surfaces for contact between the stent and adjacent tissue. FIG. 9 shows a stent 900 comprising a midbody 902 with a helical thread 910, a first flange 904 and a second flange 906, and at least one additional flange 964 situated between one or more of the flanges 904, 906 and the midbody 902, which also includes a textured surface 966 disposed in the interthread space 912. Without being bound to or limited by a particular theory, including one or more such flanges in a stacked fashion may provide enhanced resistance to stent migration as compared to an isolated flange, in that the flanges in a stacked flange design provide additional support to their adjacent flanges. In some embodiments, the same number of additional flanges 964 may be included adjacent to each end. Alternatively, as shown in FIG. 9, more additional flanges 964 can be included adjacent to one end as compared to the other.

Figure 10A:
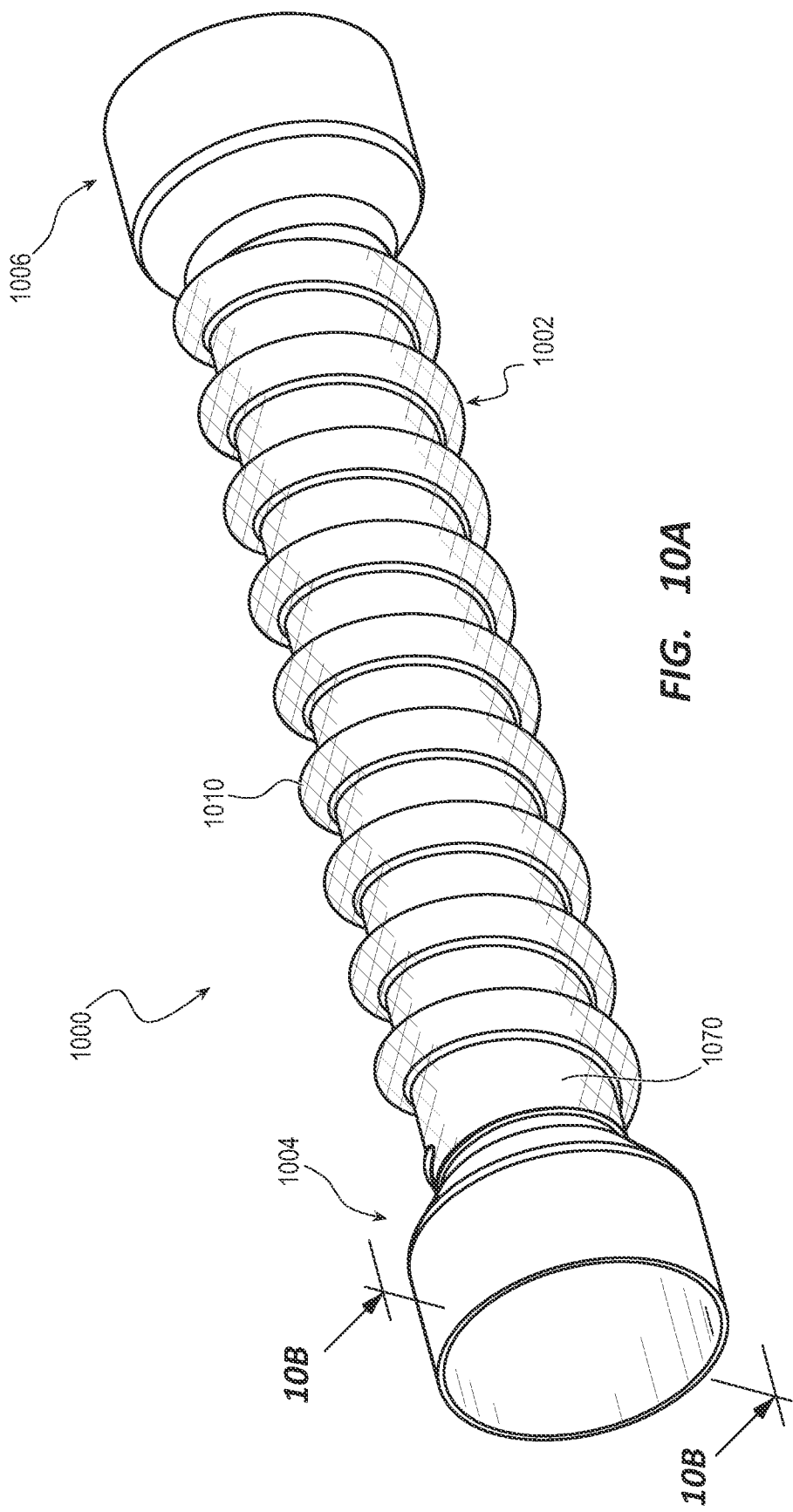
FIG. 10A is a perspective view of a stent assembly in accordance with another embodiment.
Figure 10B:
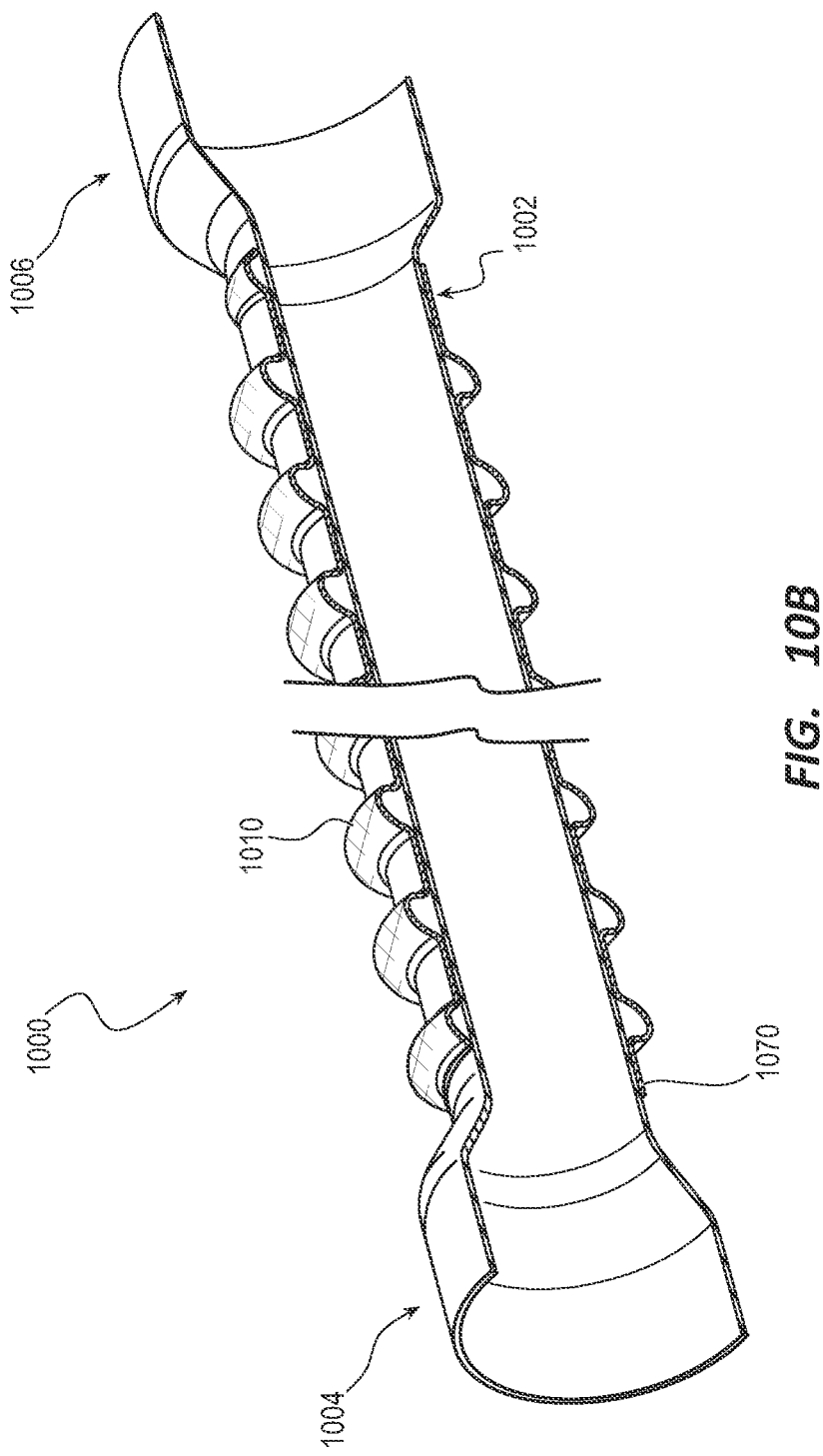
FIG. 10B is a cross-sectional view of the stent shown in FIG. 10A taken on the plane indicated in FIG. 10A as 10B.

FIG. 10A and FIG. 10B show another embodiment of stent assembly 1000 in accordance with the present disclosure, where FIG. 10B represents a cross-sectional view taken at the plane "10B" shown in FIG. 10A. The stent assembly 1000 comprises inner and outer components, the inner component being a stent having a midbody 1002, a first end 1004, and a second end 1006, and the outer component being a tubular sleeve 1070 surrounding at least part of the midbody 1002 and comprising a helical thread 1010. In some embodiments, as illustrated by stent assembly 1000, the sleeve 1070 and the midbody 1002 can be of a similar length, such that the sleeve 1070 surrounds substantially the entire length of the midbody 1002. In some embodiments, the sleeve has a length substantially shorter than the midbody.

The sleeve can serve to confer a feature or property on a portion of a stent that may be absent elsewhere on the stent. For example, an inner cylindrical sleeve can be used to anchor a unique feature, e.g. an anti-reflux valve. In another example, an outer threaded sleeve can be disposed over a portion of the length of the stent to provide added migration resistance and/or axial strength to that specific portion. This can be of benefit where the lumen in which the stent is placed has varying anatomical characteristics. Accordingly, in some embodiments, the sleeve is fixedly secured to the stent so that there is little to no movement of one component relative to the other. In other embodiments, the sleeve is configured to allow movement of the stent relative to the sleeve. In certain embodiments, the sleeve and/or the stent are configured so that such movement is limited or to otherwise maintain a connection between the sleeve and the stent. In certain embodiments, one or both ends of the stent can include flanges or other structures that limit the relative movement between the stent and the sleeve.

In some embodiments, the stent and the sleeve can be constructed from or include different materials. For example, in some embodiments, the stent can include a cover to provide the benefits discussed above, while at least a portion of the sleeve does not include a cover. An aspect of such an arrangement is that benefits of a cover can be realized, e.g., smoother flow of matter through the interior space of the stent and/or greater ease of removal, while also realizing benefits of uncovered material, e.g., enhanced migration resistance through tissue ingrowth.

As discussed above, structural considerations can influence the placement method (e.g., "through-the-scope" or "over the wire") for which stents described herein are suited. Stents designed for "over the wire" placement can include wires having significantly larger diameters. In some embodiments, the two-layer assembly is designed for use in "over the wire" placement based on the amount of material involved in their construction.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the terms "substantially" and "about." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration. All ranges also include both endpoints.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A stent comprising:
   a tubular body having a longitudinal axis, a midbody extending between a first end and a second end, and a helical thread circumferentially arranged on an outer surface of the midbody, wherein the helical thread comprises a plurality of turns and an interthread space,
   wherein the interthread space defines an interior space of the midbody having a cylindrical profile and having a profile diameter, and wherein the helical thread protrudes radially from the cylindrical profile at a thread height that is from about 2.5% to about 30% of the profile diameter.

2. The stent of claim 1, wherein the interthread space has a constant length.

3. The stent of claim 1, wherein the interthread space has a length that varies.

4. The stent of claim 1, wherein the tubular body comprises a mesh structure.

5. The stent of claim 1, further comprising a cover coupled to the tubular body.

6. The stent of claim 1, wherein the thread height is from about 0.5 mm to about 5 mm.

7. The stent of claim 1, wherein the helical thread has a cross-sectional profile shape selected from a circle, an ellipse, or a triangle.

8. The stent of claim 7, wherein the cross-sectional profile shape is an isosceles triangle.

9. The stent of claim 7, wherein the cross-sectional profile shape is a buttress shape comprising:
   a thrust face oriented at a first angle from perpendicular to the longitudinal axis, and
   a bracing face oriented at a second angle from perpendicular to the longitudinal axis, where the second angle is greater than the first angle.

10. The stent of claim 1, wherein the helical thread extends onto at least one of the first end and second end.

11. The stent of claim 1, wherein at least one of the first end and second end is a flange having a diameter greater than a diameter of the midbody.

12. The stent of claim 11, further comprising one to three additional flanges situated between the end and the midbody.

13. The stent of claim 1, further comprising a textured surface disposed over the entirety of the tubular body or a designated portion thereof.

14. The stent of claim 13, wherein the textured surface is a micropatterned surface.

15. The stent of claim 13, wherein the designated portion thereof is selected from the helical thread or the interthread space.

16. A stent comprising:
   a tubular body having a longitudinal axis, a midbody extending between a first end and a second end, and a helical thread circumferentially arranged on an outer surface of the midbody, wherein the helical thread comprises a plurality of turns and an interthread space, and wherein the helical thread has a cross-sectional profile shape comprising a buttress shape comprising:
      a thrust face oriented at a first angle from perpendicular to the longitudinal axis, and
      a bracing face oriented at a second angle from perpendicular to the longitudinal axis, where the second angle is greater than the first angle.

17. The stent of claim 16, wherein the interthread space has a constant length.

18. The stent of claim 16, wherein the interthread space has a length that varies.

19. The stent of claim 16, wherein the helical thread extends onto at least one of the first end and second end.

20. The stent of claim 16, wherein at least one of the first end and second end is a flange having a diameter greater than a diameter of the midbody.

* * * * *